(12) United States Patent
Hori et al.

(10) Patent No.: US 9,162,081 B2
(45) Date of Patent: Oct. 20, 2015

(54) BEAM MONITOR SYSTEM AND PARTICLE BEAM IRRADIATION SYSTEM

(71) Applicant: HITACHI, LTD., Tokyo (JP)

(72) Inventors: Yoshihito Hori, Tokyo (JP); Takayoshi Matsushita, Tokyo (JP); Kunio Moriyama, Tokyo (JP); Masahiro Tadokoro, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/548,556

(22) Filed: Nov. 20, 2014

(65) Prior Publication Data

US 2015/0151140 A1 Jun. 4, 2015

(30) Foreign Application Priority Data

Dec. 2, 2013 (JP) .................. 2013-248881

(51) Int. Cl.
| | |
|---|---|
| H01J 37/02 | (2006.01) |
| A61N 5/00 | (2006.01) |
| H01J 29/41 | (2006.01) |
| A61N 5/10 | (2006.01) |
| G01T 1/29 | (2006.01) |

(52) U.S. Cl.
CPC ............ *A61N 5/1065* (2013.01); *A61N 5/1077* (2013.01); *G01T 1/2935* (2013.01); *A61N 2005/1074* (2013.10)

(58) Field of Classification Search
CPC . A61N 5/1043; A61N 5/1075; A61N 5/1071; A61N 5/1049; A61N 5/1064; A61N 5/1065; G01T 1/29; G01T 1/2935; H01J 29/41; H01J 37/02; H01J 37/243

USPC ....... 250/397, 492.3, 396 R, 398, 491.1, 305, 250/492.1
See application file for complete search history.

(56) References Cited

U.S. PATENT DOCUMENTS

| | | | | |
|---|---|---|---|---|
| 5,039,861 | A * | 8/1991 | Swenson ........................ | 250/397 |
| 8,674,319 | B2 * | 3/2014 | Iwamoto et al. ............... | 250/397 |
| 9,044,605 | B2 * | 6/2015 | Hori et al. ...................... | 1/1 |
| 2012/0305796 | A1 * | 12/2012 | Iseki et al. ................ | 250/396 R |
| 2015/0041665 | A1 * | 2/2015 | Hollebeek et al. ............ | 250/375 |

OTHER PUBLICATIONS

Chu et al., "Instrumentation for treatment of cancer using proton and light-ion beams", Review of Scientific Instruments, Aug. 1993, pp. 2074-2093, vol. 64, No. 8.

* cited by examiner

*Primary Examiner* — David A Vanore
(74) *Attorney, Agent, or Firm* — Mattingly & Malur, PC

(57) ABSTRACT

A beam monitor system having a simple configuration for improving a measurement precision specifying a position and the width. A beam monitor system, comprising collection electrodes that include a plurality of groups each having a plurality of adjacent wire electrodes, and detect an ionized particle beam passing therethrough, a first signal processing device that sets one wire electrode in the groups of the collection electrodes as a typical wire electrode, receives a detection signal output from the typical wire electrode to process the signal and a beam monitor controller that obtains a beam position of the ionized particle beam that has passed through the wire electrodes on the basis of a processed signal from the first signal processing device.

10 Claims, 7 Drawing Sheets

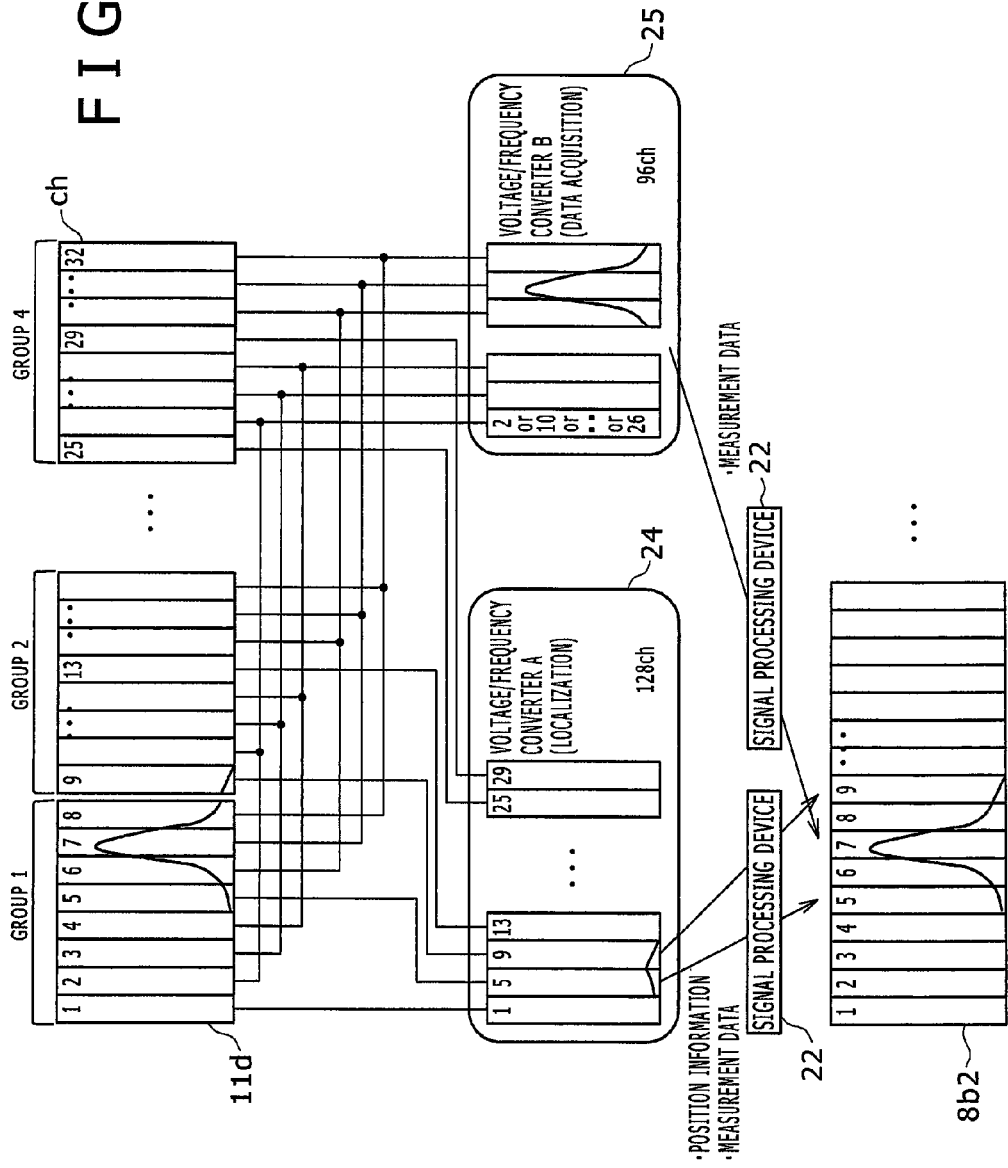

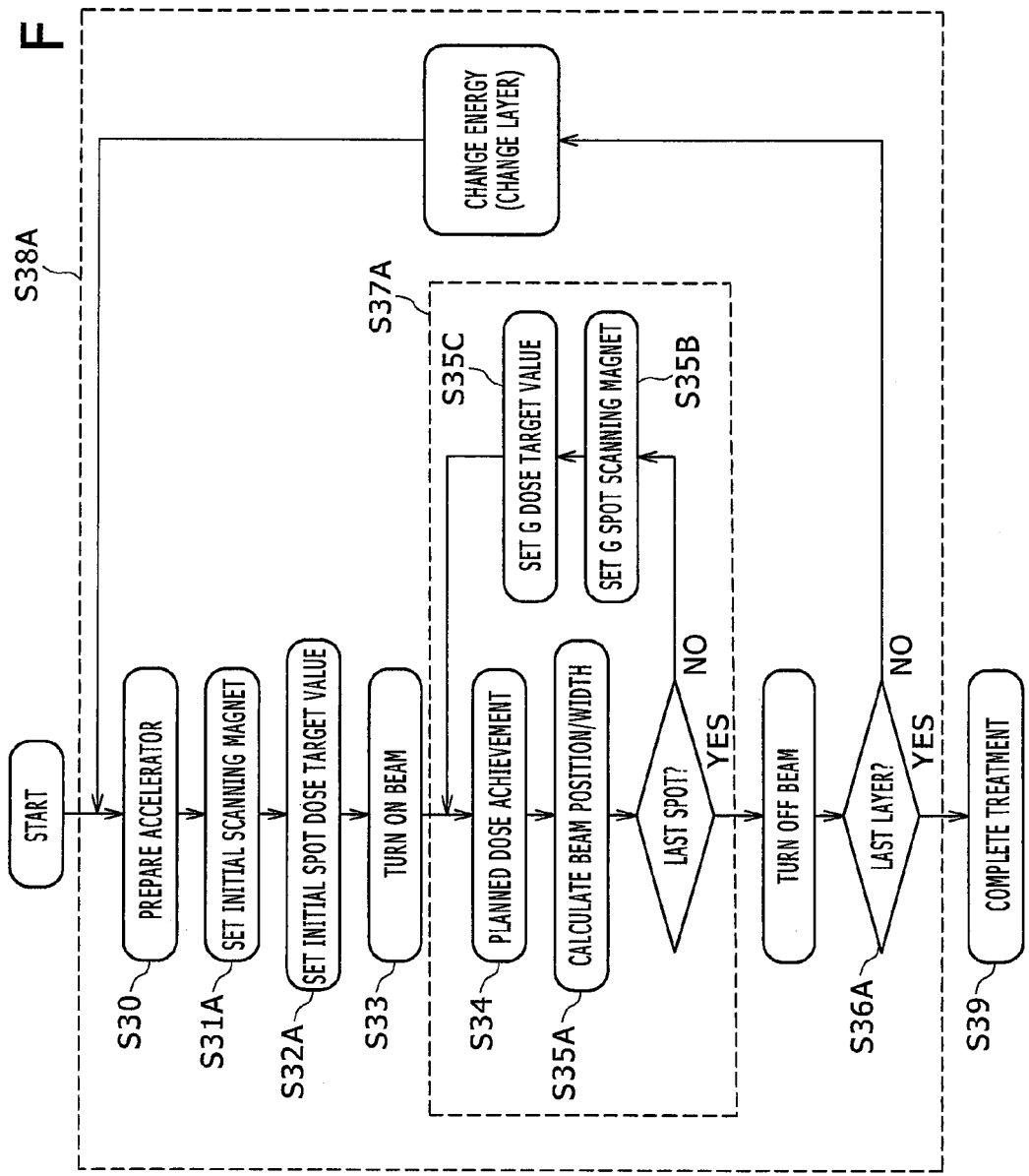

BEAM MONITOR SYSTEM AND PARTICLE BEAM IRRADIATION SYSTEM

BACKGROUND

The present invention relates to a monitor system of a beam position in an irradiation system of a charged particle beam (particle beam, ion beam), and more particularly to a beam monitor system in a particle beam irradiation system suitably applied to a particle beam therapy device that irradiates an affected area with a particle beam such as protons or carbon ions for treatment.

A treatment method has been known which irradiates an affected area of a patient suffering from cancer with an ionized particle beam such as protons or carbon ions. An ionized particle beam irradiation system (particle beam extraction device or ionized particle beam extraction device) used for the treatment includes an ionized particle accelerator. An ion beam accelerated by the ionized particle accelerator reaches an irradiation device installed in a rotating gantry through a first beam transportation system and a second beam transportation system disposed in the rotating gantry. The ion beam is extracted from an irradiation device, and exposed to the affected area of the patient.

As irradiation systems of the irradiation device, there have been known, for example, a double scattering system (p. 2081, FIG. 35 of "REVIEW OF SCIENTIFIC INSTRUMENTS, VOLUME. 64, NUMBER 8, (August 1993), P2074-2093") that scatters a beam by a scatterer, and broaches the beam into an affected area shape as disclosed in "REVIEW OF SCIENTIFIC INSTRUMENTS, VOLUME. 64, NUMBER 8, (August 1993), P2074-2093", a wobbler method (p. 2084, FIG. 41 of "REVIEW OF SCIENTIFIC INSTRUMENTS, VOLUME. 64, NUMBER 8, (August 1993), P2074-2093", and a scanning system (pp. 2092 and 2093 of "REVIEW OF SCIENTIFIC INSTRUMENTS, VOLUME. 64, NUMBER 8, (August 1993), P2074-2093") that scans the affected area with a fine beam.

SUMMARY

In the above beam irradiations, attention has been paid to the scanning system from the viewpoint that the system hardly affects normal cells, and requires no nozzle built-in equipment. The scanning system stops an output of the ionized particle beam in correspondence with the amount of irradiation to an irradiation target, controls energy and a scanning magnet to change an irradiation position of the ionized particle beam called "spot", and restarts the extraction of the ionized particle beam after completion of the change to apply the beam along a shape of an irradiation target (affected area) while sequentially switching the irradiation position to another.

In the charged particle irradiation system, in order to apply the charged particle along the shape of the affected area, a beam position monitor (hereinafter referred to as "spot position monitor") is installed on a downstream side of the scanning magnet, and immediately before the patient to be irradiated.

The spot position monitor is a system configured by a detector (hereinafter referred to as "channel") called "multilayer", accumulates the amount of charge generated by passage of the beam for each of the channels in a capacitor, and reads an induced voltage. Since a signal detected in each channel is weak, an amplifier is installed on a downstream side of the channel, a signal detected by the channel is transmitted to a signal processing device through the amplifier to detect a position and a width of the beam.

A measurement wire interval of a related art beam monitor as disclosed in "REVIEW OF SCIENTIFIC INSTRUMENTS, VOLUME. 64, NUMBER 8, (August 1993), P2074-2093" is wide, and in order to enhance a measurement precision specifying the position and the width, there is a need to narrow the interval of the measurement wire, and increase the number of measurement points. For that reason, there arises such a problem that the related art spot position monitor increases the costs because the signal amplifier and the signal processing device are required in association with the number of channels, and a monitor system must be larger-scaled and more complicated in configuration as the number of channels increases more in order to conduct signal amplification and signal processing on all of the channels for detection of the position and the width of the beam.

An object of the present invention is to provide a beam monitor system having a simple configuration for improving the measurement precision specifying the position and the width in the spot irradiation of the scanning system, and a particle beam irradiation system including the beam monitor system.

In order to solve the above problem, for example, configuration defined in the claims is applied.

The present invention includes plural means for solving the above problem, and as one example, includes collection electrodes that include a plurality of groups each having a plurality of adjacent wire electrodes, and detect an ionized particle beam passing therethrough; a first signal processing device that sets one wire electrode in the groups of the collection electrodes as a typical wire electrode, receives a detection signal output from the typical wire electrode to process the signal; and a beam monitor controller that obtains a beam position of the ionized particle beam that has passed through the wire electrodes on the basis of a processed signal from the first signal processing device.

According to the present invention, in the beam monitor system having a large number of measurement wires, a system for precisely detecting a position and the width of the beam irradiation can be realized with a simple configuration. Also, because the beam irradiation position can be specified by only the measurement value as in the related art monitor, the irradiation position can be specified immediately even at the time of an error beam irradiation, and an accurate irradiation position can be specified without requiring complicated processing.

BRIEF DESCRIPTION OF THE DRAWINGS

FIG. 6 is a diagram illustrating an outline of a distribution determination related to a beam monitor in the beam monitor system of the particle beam irradiation system according to the first embodiment of the present invention; and FIG. 7 is a flowchart of a control of the ionized particle beam irradiation by a raster scanning system.

DETAILED DESCRIPTION

Hereinafter, a description will be given of a beam monitor system and a particle beam irradiation system according to an embodiment of the present invention with reference to the accompanying drawings.

First Embodiment

A description will be given of a beam monitor system and a particle beam irradiation system according to a first embodiment of the present invention with reference to FIGS. 1 to 6.

In the present invention, the particle beam irradiation system means a system that irradiates an affected area of a patient fixed on a couch (bed device) 10 within a treatment room with an ionized particle beam 12 (for example, proton, heavy ion beam, or the like).

First, a configuration of the particle beam irradiation system according to the present invention will be described with reference to FIGS. 1 to 3.

Figure 1:
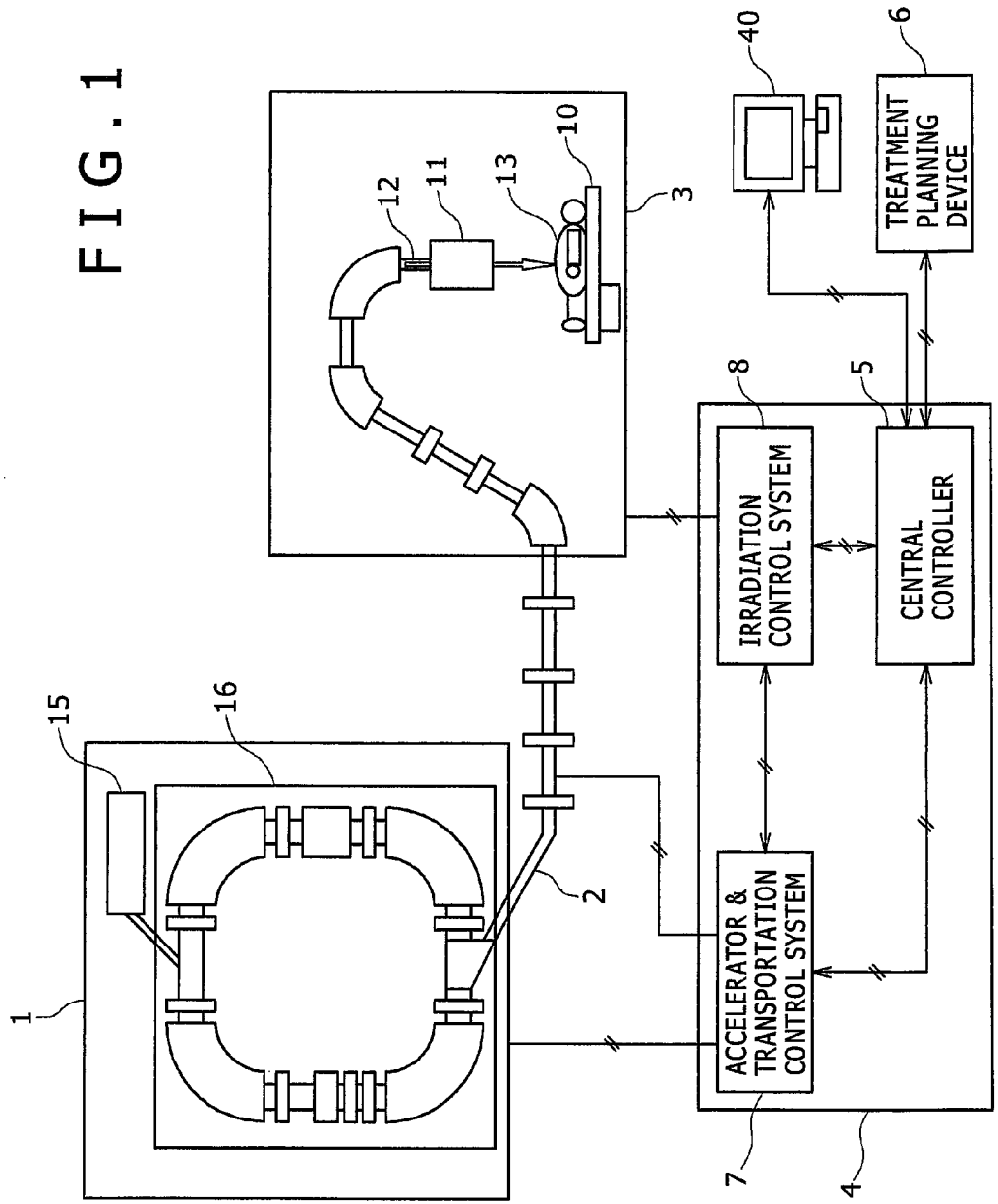
FIG. 1 is a configuration diagram illustrating an overall configuration of a particle beam irradiation system according to a first embodiment of the present invention.
Figure 2:
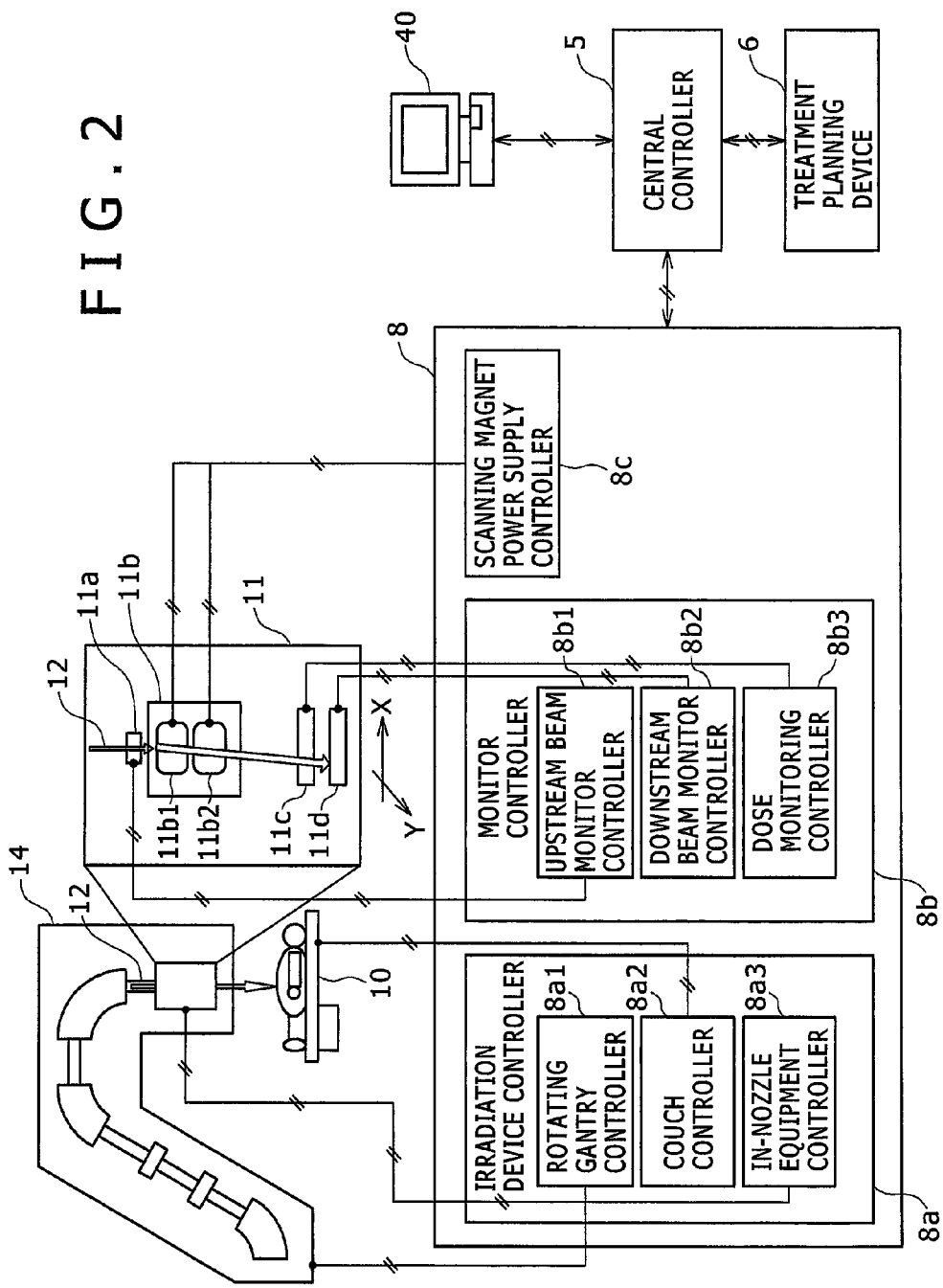
FIG. 2 is a configuration diagram illustrating an outline of a scanning irradiation system and an irradiation control system in the particle beam irradiation system according to the first embodiment of the present invention.
Figure 3:
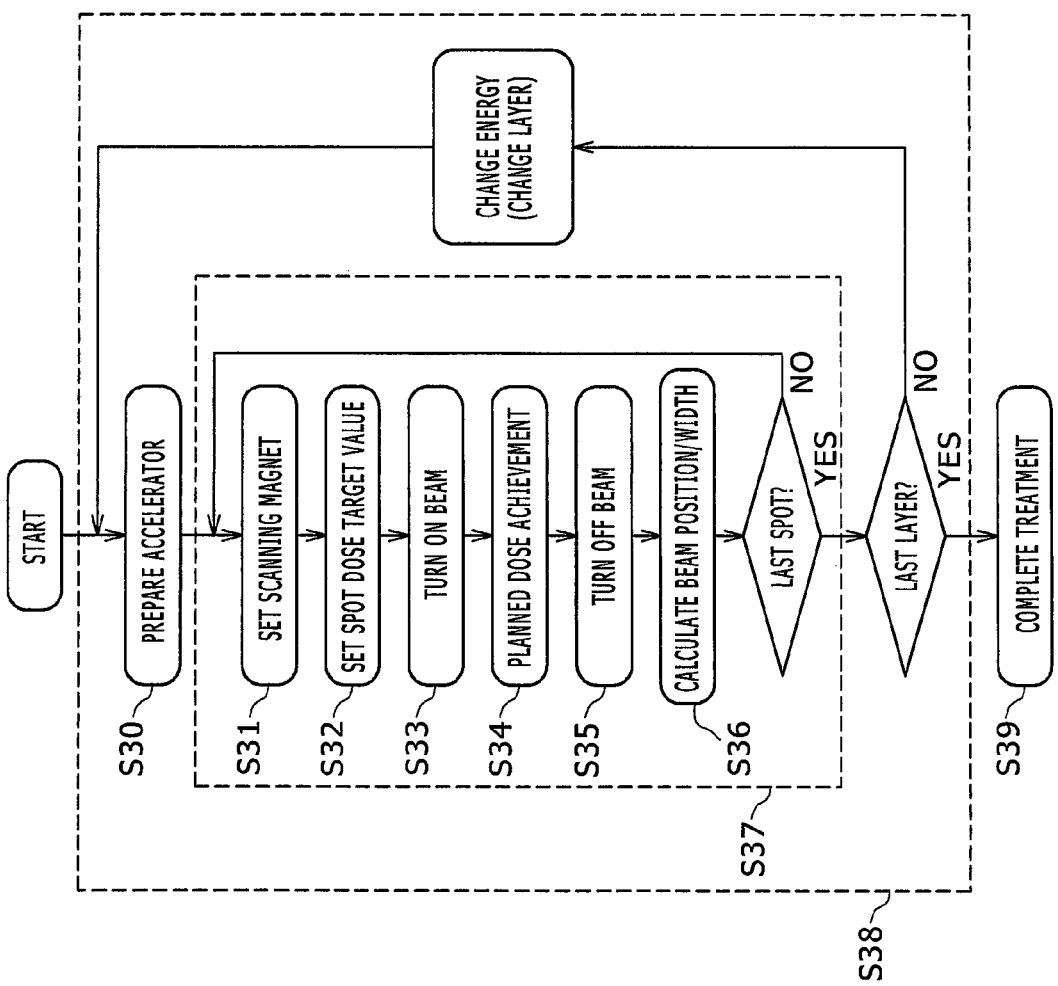
FIG. 3 is a flowchart of a control of the ionized particle beam irradiation by the scanning irradiation system.

FIG. 1 is a configuration diagram of this embodiment, FIG. 2 is a configuration diagram of a scanning irradiation device configuring an ionized particle beam irradiation system according to this embodiment, and FIG. 3 is a flowchart of a control of the ionized particle beam irradiation by the scanning irradiation system.

Referring to FIG. 1, the particle beam irradiation system according to this embodiment generally includes an ionized particle beam generator 1, a beam transportation system 2, a scanning irradiation device 3, and a control system 4.

The ionized particle beam generator 1 includes an ion source (not shown), an initial accelerator 15, and a synchrotron accelerator (synchrotron accelerator) 16. In this embodiment, as the synchrotron accelerator 16, a synchrotron accelerator will be exemplified, but another accelerator such as a cyclotron accelerator may be employed. An ion source is connected to an upstream side of the initial accelerator 15, and the synchrotron accelerator 16 is connected to a downstream side of the initial accelerator 15.

The beam transportation system is connected to a downstream side of the ionized particle beam generator 1, and connects the ionized particle beam generator 1 to the scanning irradiation device 3.

The scanning irradiation device 3 irradiates an affected area of a patient with the ionized particle beam 12, and as illustrated in FIG. 2, generally includes a couch 10 on which a patient 13 is placed, an irradiation nozzle (nozzle device) 11, and a rotating gantry 14.

The couch 10 is arranged within a treatment room, allows the patient 13 to be placed thereon, and positions the affected area.

As illustrated in FIG. 2, an upstream beam monitor 11a, a scanning magnet 11b, a dose monitor 11c, and a downstream beam monitor 11d are arranged along a beam path in order in the irradiation nozzle 11 from an upstream side in a traveling direction of the ionized particle beam 12. The irradiation nozzle 11 forms an irradiation boundary of the scanning beam.

The upstream beam monitor 11a measures a passing position and a beam width (beam diameter) of the ionized particle beam 12 entering the irradiation nozzle 11.

The scanning magnet 11b includes a first scanning magnet 11b1 that deflects and scans the ionized particle beam passing therethrough in a first direction (for example, an X-axis direction), and a second scanning magnet 11b2 that deflects and scans the ionized particle beam in a second direction (for example, a Y-axis direction) perpendicular to the first direction. In this example, the X-axis direction is one direction within a plane perpendicular to the traveling direction of the ionized particle beam entering the irradiation nozzle 11, and the Y-axis direction indicates a direction perpendicular to the X-axis within the plane.

The dose monitor 11c measures an irradiation dose of the ionized particle beam passing therethrough. That is, the dose monitor 11c monitors the irradiation dose of the ionized particle beam with which the patient is irradiated.

The downstream beam monitor 11d is installed on a downstream side of the scanning magnet 11b, and measures a position and a beam width of the ionized particle beam passing therethrough. That is, the downstream beam monitor 11d measures the position and the beam width of the ionized particle beam scanned by the scanning magnet 11b.

The rotating gantry 14 is configured to be rotatable about an isocenter (not shown), and determine an irradiation angle of the beam. The rotation of the rotating gantry 14 enables the irradiation angle of the ionized particle beam 12 with which the couch 10 is irradiated to be changed.

As illustrated in FIG. 1, the control system 4 generally includes a central controller 5, an accelerator & transportation control system 7 and an irradiation control system 8.

The central controller 5 is connected to a treatment planning device 6, the accelerator & transportation control system 7, and the irradiation control system 8, and an operation terminal 40. The central controller 5 has a function of calculating a set value of an operating parameter for operating the accelerator, operation parameters for forming the irradiation boundary, and set values of a planned beam position, a beam width, and doze on the basis of set data from the treatment planning device 6. The operating parameters and the monitor set values are output from the central controller 5 to the accelerator & transportation control system 7 and the irradiation control system 8.

The accelerator & transportation control system 7 is connected to the ionized particle beam generator 1 and the beam transportation system 2, and controls an equipment configuring the ionized particle beam generator 1 and the beam transportation system 2.

The irradiation control system 8 is connected to the scanning irradiation device 3, and controls an equipment configuring the scanning irradiation device 3.

The operation terminal 40 includes an input device that inputs data or a request signal by an operator (health care workers such as a doctor or an operator), and a display screen.

The irradiation control system 8 will be described with reference to FIG. 2.

The irradiation control system 8 includes an irradiation device controller 8a, a monitor controller 8b, and a scanning magnet power supply controller 8c.

The irradiation device controller 8a includes a rotating gantry controller 8a1 that controls the respective equipments configuring the rotating gantry 14, a couch controller 8a2 that moves the couch 10, and controls positioning of the couch 10, and a nozzle built-in equipment controller 8a3 that controls the equipments arranged within the nozzle 11. In those components, the rotating gantry controller 8a1 controls a rotating angle of the rotating gantry 14 to control an irradiation angle of the ionized particle beam with which the patient 13 is irradiated.

The monitor controller 8b includes an upstream beam monitor controller 8b1 that controls the upstream beam monitor 11a, a downstream beam monitor controller 8b2 that controls the downstream beam monitor 11d, and a dose monitor controller 8b3 that controls the dose monitor 11c.

The upstream beam monitor controller 8b1 has a function of measuring a beam position and a beam width of the ionized particle beam entering the upstream beam monitor 11a, and a function (error detection processing) of determining whether an error is present in the ionized particle beam, or not.

The downstream beam monitor controller 8b2 has a function of measuring the beam position and the beam width of the ionized particle beam scanned by the scanning magnet 11b, and entering the downstream beam monitor 11d. That is, the downstream beam monitor controller 8b2 has a function (error detection processing) of determining whether an error is present in the beam position and the beam width of the scanned ionized particle beam, or not. The functions of the upstream beam monitor controller 8b1 and the downstream beam monitor controller 8b2 will be described in detail below.

The upstream beam monitor controller 8b1 receives measurement data measured by the upstream beam monitor 11a to process the signal, and obtains the position through which the ionized particle beam passes, and the beam width. If the obtained beam position falls outside a predetermined range, or the obtained beam width falls outside a predetermined range, the upstream beam monitor controller 8b1 determines that an error is present in the beam, and outputs an error signal to the central controller 5.

The downstream beam monitor controller 8b2 receives the measurement data measured by the downstream beam monitor 11d to process the measurement data, and obtains the position through which the ionized particle beam passes, and the beam width. If the obtained beam position falls outside a predetermined range, or the obtained beam width falls outside a predetermined range, the downstream beam monitor controller 8b2 determines that an error is present in the beam, and outputs an error signal to the central controller 5.

The central controller 5 receives the error signal from the upstream beam monitor controller 8b1 or the downstream beam monitor controller 8b2, the central controller 5 outputs a beam stop request signal to the accelerator & transportation control system 7, and stops the ionized particle beam extracted from the ionized particle beam generator 1.

In this embodiment, the ionized particle beam extracted from the ionized particle beam generator 1 stops under control. Alternatively, the central controller 5 may control the beam transportation system 2, and stop the ionized particle beam entering the irradiation nozzle 11 under the control.

In this example, the beam position of the ionized particle beam represents, for example, a position of the center of gravity of the ionized particle beam passing through, for example, a beam monitor (upstream beam monitor 11a or dose monitor 11c).

Also, the beam width of the ionized particle beam represents an area of the ionized particle beam passing through the beam monitor (upstream beam monitor 11a or dose monitor 11c). As how to obtain the beam width, there are, for example, a method of calculating an area in which the ionized particle beam is detected by a beam monitor (upstream beam monitor 11a or dose monitor 11c) placed on a plane perpendicular to the beam traveling direction, and a method of calculating an area of a detection region of the ionized particle beam in the above beam monitor, and the width of the detection region.

The scanning magnet power supply controller 8c controls a power supply device (not shown) of the scanning magnet 11b to control an excitation current excited in a scanning magnet 11b, and changes an irradiation position of the ionized particle beam onto the patient 13.

Subsequently, a description will be given of a flow from a treatment start to a treatment end of the patient with reference to FIG. 3.

In this embodiment, a description will be given of an example of scanning irradiation in which an affected area of the patient 13 is divided into plural layers along a beam traveling direction (a depth direction from a body surface of the patient 13), each of the layers is divided into small regions which are plural spots, and irradiated with a beam.

The treatment planning device 6 stores a treatment plan of the patient which has been acquired in advance therein. The treatment plan includes irradiation data (beam energy information, irradiation position information, target dose values of the ionized particle beam at the respective irradiation positions), and tolerance data (allowable beam position information and allowable beam width information in the upstream beam monitor 11a, and allowable beam position information and allowable beam width information at the respective irradiation positions in the downstream beam monitor 11d).

In this embodiment, the treatment planning device 6 obtains the irradiation data and the tolerance data. Alternatively, the treatment planning device 6 may obtain the irradiation data, and the central controller 5 may obtain the tolerance data. In this case, the treatment planning device 6 transmits data necessary for obtaining the tolerance data to the central controller 5, and the central controller 5 calculates the tolerance data on the basis of the received data. The target dose value which is the irradiation data is determined at each of the spot positions within each of the layers.

When the patient 13 is fixed onto the couch (bed), the doctor inputs a preparation start signal from an input device of the operation terminal 40.

The central controller 5 that receives the preparation start signal receives the treatment plan of an appropriate patient from the treatment planning device 6, and outputs bed position information to the couch controller 8a2. The couch controller 8a2 moves and positions the couch 10 on the basis of the bed position information so as to arrange the patient 13 at a given position on an extension of a beam axis. Also, the central controller 5 outputs gantry angle information to the rotating gantry controller 8a1. The rotating gantry controller 8a1 rotates the rotating gantry 14 on the basis of the gantry angle information, and arranges the rotating gantry 14 at a given angle. Also, the central controller 5 transmits the target dose value and the tolerance data of the ionized particle beam for each of the irradiation positions to the monitor controller 8b. The central controller 5 calculates the excitation current value to be excited in the scanning magnet 11b on the basis of beam energy information and irradiation position information included in the irradiation data, obtains the excitation current parameter, and transmits the excitation current parameter to the scanning magnet power supply controller 8c. Further, the central controller 5 obtains the operating parameter for accelerating operation of the synchrotron accelerator 16, and the operating parameters of the beam transportation system 2 for transporting the ionized particle beam extracted from the synchrotron accelerator 16 to the irradiation nozzle 11 on the basis of the treatment plan. Then, the central controller 5 transmits those operating parameters to the accelerator & transportation control system 7.

Upon the completion of preparation of the treatment, the doctor inputs the treatment start signal to the central controller 5 from the input device of the operation terminal 40.

The central controller 5 that receives the treatment start signal transmits a command signal to the accelerator & transportation control system 7.

Then, the accelerator & transportation control system 7 sets the operating parameters corresponding to a layer (first beam energy information) first irradiated for the synchrotron accelerator 16 and the beam transportation system 2. When the operating parameters of the synchrotron accelerator 16 and the beam transportation system 2 are set to complete the operation start preparation (Step S30), the scanning magnet power supply controller 8c excites the scanning magnet 11b on the basis of the excitation current parameter (Step S31). After the excitation current corresponding to a first irradiation spot has been excited in the scanning magnet 11b, the dose monitor controller 8b3 of the monitor controller 8b starts to monitor the irradiation dose on the basis of the target dose value for the spot position (Step S32), and completes pre-irradiation.

When the central controller 5 transmits a beam extraction start command (Step S33), the accelerator & transportation control system 7 starts the ion source, and generates charged particles (protons or heavy particles). The initial accelerator 15 accelerates the charged particles from the ion source, and extracts the charged particles to the synchrotron accelerator 16. The synchrotron accelerator 16 further accelerates the ionized particle beam. The orbiting ionized particle beam is accelerated to target energy, and extracted from the synchrotron accelerator 16 to the beam transportation system 2. The ionized particle beam reaches the scanning irradiation device 3 through the beam transportation system 2. The ionized particle beam travels within the irradiation nozzle 11 along the beam axis, and passes through the upstream beam monitor 11a, the scanning magnet 11b, the dose monitor 11c, and the downstream beam monitor 11d. The affected area of the patient 13 is irradiated with the ionized particle beam extracted from the irradiation nozzle 11.

The dose monitor controller 8b3 receives the measurement data measured by the dose monitor 11c to process the measurement data, and obtains the irradiation dose of each irradiation spot. The dose monitor controller 8b3 continues the irradiation of the ionized particle beam until the irradiation dose value of a first irradiation spot reaches a target dose value. If the dose monitor controller 8b3 determines that the irradiation dose value reaches the target dose value, the dose monitor controller 8b3 outputs an irradiation completion signal to the central controller 5 (Step S34). Upon receiving the irradiation completion signal, the central controller 5 stops the irradiation of the ionized particle beam (Step S35).

Then, first detection data detected by the upstream beam monitor 11a is captured by the upstream beam monitor controller 8b1, and second detection data detected by the downstream beam monitor 11d is captured by the downstream beam monitor controller 8b2. Then, the position and the beam width of the irradiated ionized particle beam are obtained (Step S36).

The arithmetic processing is completed, and if no error is present in the position and the beam width of the beam (if it is determined that the beam position falls within the allowable beam position, and the beam width falls within the allowable beam width), it is determined whether the irradiation spot of irradiation expired is a last spot position within the layer, or not. If it is determined that the irradiation spot of irradiation expired is not the last spot position (no), the flow returns to Step S31, and the scanning magnet power supply controller 8c changes the excitation current value of the scanning magnet 11b so as to irradiate a next spot with the ionized particle beam.

When the scanning magnet power supply controller 8c excites the scanning magnet 11b on the basis of the excitation current parameter (Step S31), the dose monitor controller 8b3 of the monitor controller 8b restarts to monitor the beam dose on the basis of the target dose value of the next irradiation spot position (Step S32). Thereafter, when the central controller 5 transmits a beam extraction start command, the irradiation of the next irradiation spot position with the ionized particle beam starts (Step S33).

The control flow (Step S37) from the scanning magnet setting (Step S31) to the determination of whether the spot is last, or not, is repetitively conducted until it is determined that the irradiation spot of irradiation expired is the last spot position within the layer (until determination of "yes").

If the irradiation of all the spots within the layer has been completed, the central controller 5 determines whether the layer completely irradiated is a last layer of the patient 13, or not. If the layer is not last (no), the central controller 5 transmits a command signal to the accelerator & transportation control system 7. The accelerator & transportation control system 7 sets the operating parameter corresponding to the layer to be next irradiated for the synchrotron accelerator 16 and the beam transportation system 2, and starts a next operation preparation (Step S30).

This control flow (Step S38) is repeated until all of the layers have been completely irradiated. If all of the spots and all of the layers have been completely irradiated, the treatment is completed (Step S39).

Now, a description will be given of the measurement of the beam position and the beam width in the downstream beam monitor controller of the related art system.

In the downstream beam monitor controller, in the beam position and width measurement process, after the measurement data in the total number of channels in the downstream beam monitor has been captured, an offset in the respective channels is subtracted from the Measurement data to search a peak channel. After the search has been completed, data of N % (for example, 30%) of an output of the peak channel or lower is excluded to conduct a fitting process. Thereafter, the position and the beam width of the irradiated beam are calculated. The above processing is also applied to the upstream beam monitor controller.

In the related art system, although the channels actually necessary for calculation of the beam position and the beam width are only the channels of N % or higher of the peak channel output, data of all the channels is captured. For that reason, there is a need to install the pulse counters within the monitor signal processing device and the pulse integration devices within the downstream beam monitor controller according to the number of channels. For that reason, there arises such a problem that as the monitor system is configured by the larger number of channels than that in the related art, the number of devices must be increased as much.

The beam monitor system according to this embodiment has been found in order to solve the above problem. Hereinafter, a description will be given of the beam monitor system according to this embodiment with reference to FIGS. 4 to 6.

Figure 4:
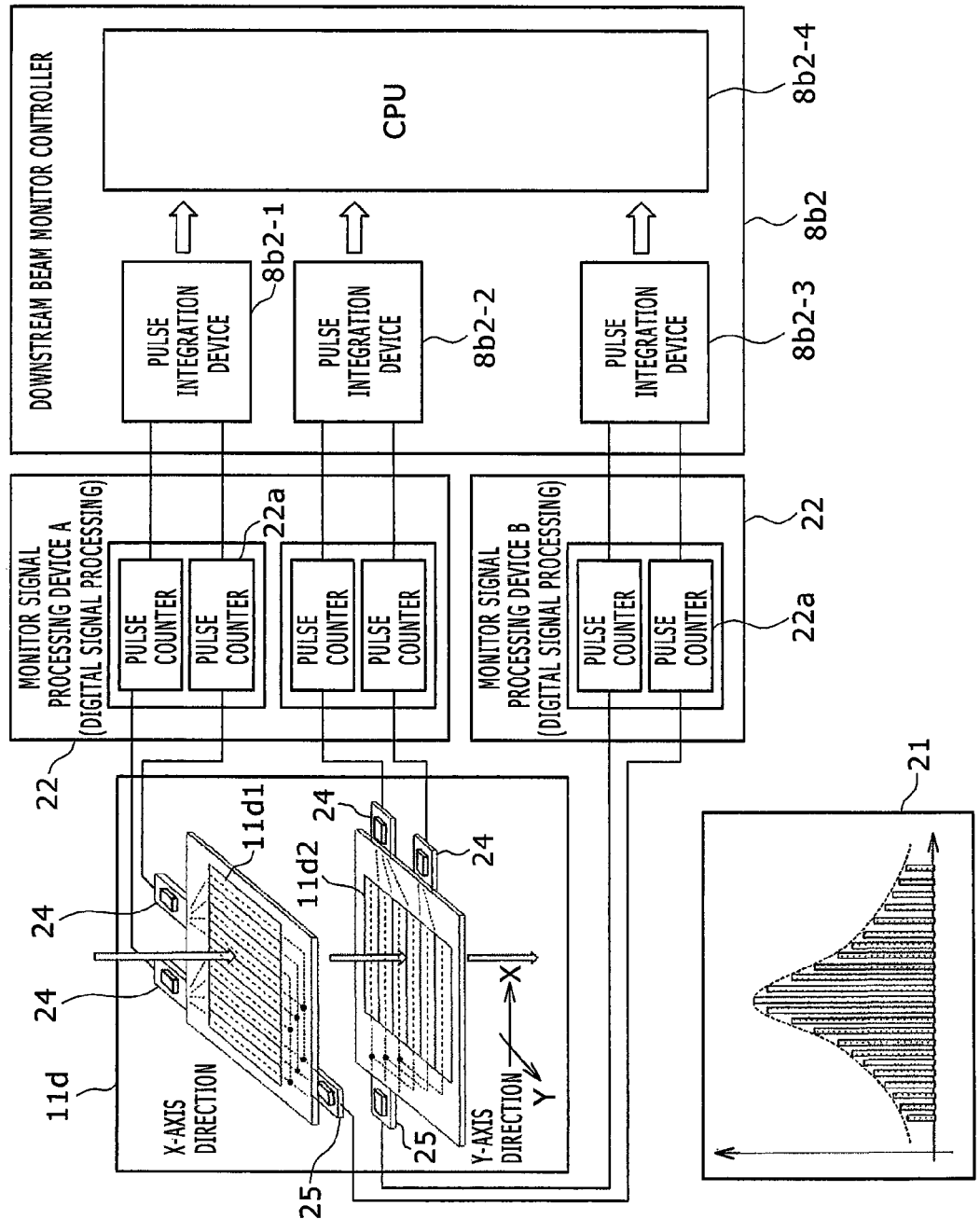
FIG. 4 is a schematic diagram of the beam monitor system in the particle beam irradiation system according to the first embodiment of the present invention.
Figure 5:
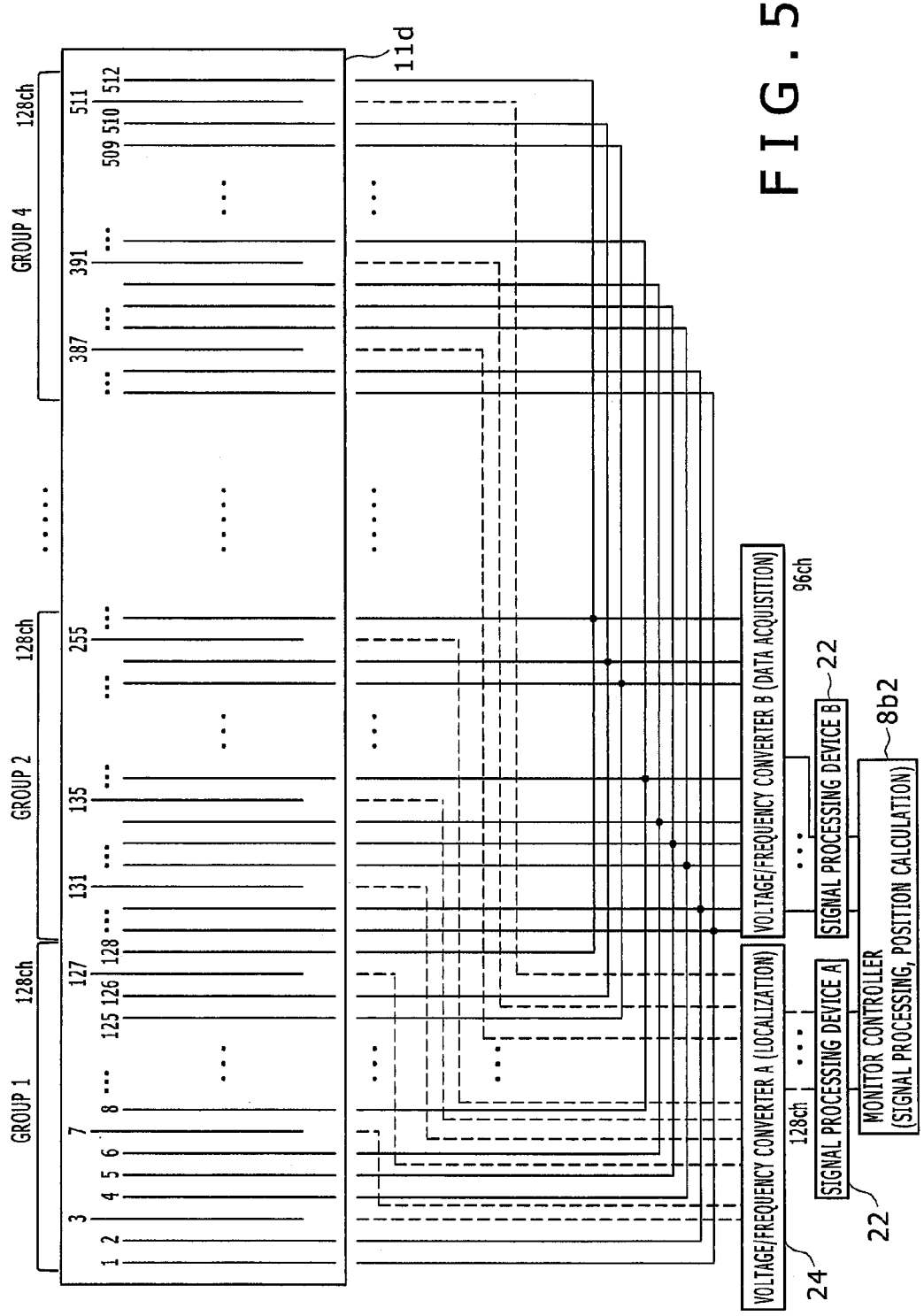
FIG. 5 is a schematic diagram illustrating an example of a connection configuration of wires in the beam monitor system of the particle beam irradiation system according to the first embodiment of the present invention.

FIG. 4 is a schematic diagram of the beam, monitor system, FIG. 5 is a diagram illustrating an example of a wire connection configuration of the high-accuracy monitor in detail, and FIG. 6 is a diagram illustrating an outline of a distribution determination related to a beam monitor in the beam monitor system.

First, the configuration of the beam monitor system will be described with reference to FIG. 4. In FIG. 4, a configuration of the downstream beam monitor system will be described as the beam monitor system. The upstream beam monitor system has the same configuration as that of the downstream beam monitor system, but is different in only the number of channels in the beam monitor from the downstream beam monitor system, and therefore the details thereof will be omitted.

In the beam monitor system according to this embodiment, as compared with the configuration of the above-mentioned related art monitor, a monitor signal processing device 22 is classified into two kinds of intended purposes for position determination and for data acquisition, and a connection of a measurement wire between the beam monitor and a voltage frequency converter is devised to provide an accurate beam position measurement performance, and a simple configuration reduced in the number of equipments is enabled.

As illustrated in FIG. 4, the downstream beam monitor 11*d* is connected to the downstream beam monitor controller 8*b*2 through the monitor signal processing device 22 that conducts digital signal processing.

The downstream beam monitor 11*d* is a multi-wire ion chamber type beam monitor. The downstream beam monitor 11*d* includes an X-electrode 11*d*1 that detects a passing position of the ionized particle beam in the X-direction, a Y-electrode 11*d*2 that detects a passing position of the ionized particle beam in the Y-direction, a high voltage electrode (voltage application electrode, not shown) that applies a voltage, and voltage/frequency converters (pulse generators) 24 and 25.

In this embodiment, a configuration in which the X-electrode and the Y-electrode are arranged in the stated order from an upstream side' in the traveling direction of the ionized particle beam is exemplified. However, the Y-electrode and the X-electrode may be arranged in stated reverse order.

Each of the X-electrode 11*d*1 and the Y-electrode 11*d*2 is formed of a charge collection electrode having a configuration in which wire electrodes (tungsten wires, etc.) are set up at regular intervals. Each of the X-electrode 11*d*1 and the Y-electrode 11*d*2 is arranged in the orbit of the ionized particle beam to detect the ionized particle beam. The voltage is applied to the high voltage electrode to generate an electric field between the X-electrode and the high voltage electrode, and generate an electric field between the Y-electrode and the high voltage electrode. When the ionized particle beam passes through the ion chamber, a gas between the high voltage electrode and the X-electrode, and a gas between the high voltage electrode and the Y-electrode are ionized, and an ion pair is generated. The generated ion pair travels to the X-electrode and the Y-electrode by the electric field, and is recovered by the wire (hereinafter referred to as "channel"). Therefore, the detected amount of charge in each of the channels is measured, thereby being capable of measuring a beam shape 21. Also, the detected amount of charge in each of the channels is processed, thereby being capable of calculating the position of the center of gravity of the beam, and the beam width.

The charge detected in each of the channels is input to the voltage/frequency converters 24 and 25. After the voltage/frequency converters 24 and 25 convert the received charge into a pulse signal, the voltage/frequency converters 24 and 25 outputs the pulse signal (detection signal) to the monitor signal processing device 22.

The monitor signal processing device 22 includes plural pulse counters 22*a*, and receives the pulse signal input from the voltage/frequency converters 24 and 25 to process the pulse signal.

Specifically, a pulse counter of the monitor signal processing device 22 integrates the number of pulses on the basis of the input pulse signals, and outputs the integrated number of pulses to integrated pulse counter capture devices 8*b*2-1, 8*b*2-2, and 8*b*2-3 of the downstream beam monitor controller 8*b*2.

In this embodiment, the functions of the voltage/frequency converter and the monitor signal processing device are newly classified into two kinds of sub-functions for position determination and data acquisition.

Specifically, as illustrated in FIG. 4, as the position determination purpose, typical wires are extracted as typical wire electrodes at intervals in order of the channels from all measurement wires of the X-electrode 11*d*1 and the Y-electrode 11*d*2. The typical wire electrodes are connected to the position determination voltage/frequency converters 24 in a one-to-one relationship, and connected to the monitor signal processing device 22 and the downstream beam monitor controller 8*b*2 in stated order.

Also, as the data acquisition purpose as illustrated in FIG. 4, the measurement wires other than the typical wire electrodes for the position determination are connected to a data acquisition voltage/frequency converter 25 in a multiple-to-one relationship, and connected to the monitor signal processing device 22, and the downstream beam monitor controller 8*b*2 in the stated order.

The downstream beam monitor controller 8*b*2 includes three pulse integration devices (first position determination pulse integration device 8*b*2-1, second position determination pulse integration device 8*b*2-2, and data acquisition pulse integration device 8*b*2-3), and a CPU 8*b*2-4.

In those components, the first position determination pulse integration device 8*b*2-1 is connected to the pulse counters 22*a* connected to the typical wire electrodes for position determination of the X-electrode, and conducts data collection by the number of pulses based on the signal detected by the typical wire electrodes in the X-electrode.

The second position determination pulse integration device 8*b*2-2 is connected to the pulse counters 22*a* connected to the typical wire electrodes for position determination of the Y-electrode, and conducts data collection by the number of pulses based on the signal detected by the typical wire electrodes in the Y-electrode.

Also, the data acquisition pulse integration device 8*b*2-3 is connected to the pulse counter connected to the wire electrodes other than the typical wire electrodes of the X-electrode or the Y-electrode, and conducts the data collection by the number of pulses based on the signal detected by the X-electrode or the Y-electrode.

Those integrated pulse counter capture devices 8*b*2-1, 8*b*2-2, and 8*b*2-3 are connected to the CPU 8*b*2-4 within the downstream beam monitor controller 8*b*2, and data (processed signals) collected by those integrated pulse counter capture devices 8*b*2-1, 8*b*2-2, and 8*b*2-3 are taken in by the CPU 8*b*2-4.

The CPU 8*b*2-4 calculates the position of the center of gravity of the ionized particle beam that has passed through the wire electrode according to the processed signal from the first position determination pulse integration device 8*b*2-1, and the second position determination pulse integration device 8*b*2-2. Also, the CPU 8*b*2-4 calculates the beam shape and the beam width of the ionized particle beam that has passed through the wire electrode according to the processed signal from the first position determination pulse integration device 8b2-1 and the second position determination pulse integration device 8b2-2, in addition to the processed signal from the data acquisition pulse integration device 8b2-3.

In this example, the beam shape of the ionized particle beam represents an intensity distribution of the beam within a plane (X-Y plane) perpendicular to the beam obit of the ionized particle beam.

Subsequently, a description will be given of a method of measuring the beam position and the beam width with the use of the downstream beam monitor 11d according to this embodiment with reference to FIGS. 5 and 6.

A configuration from the X-axis beam monitor 11d1 to the signal processing device 22 is identical with that in the Y-axis beam monitor 11d2, and therefore in this example, the X-axis beam monitor 11d1 in the downstream beam monitor 11d will be described.

In FIG. 5, in order to enhance the high accuracy of the position and the width, please let us consider a case in which the interval between the respective measurement wires is narrowed to ¼ of the interval of the related art monitor, and three wires increase between the measurement wires of the related art monitor.

As illustrated in FIG. 5, the X-axis beam monitor 11d1 is configured so that 512 wire electrodes (X-electrodes) are extended at regular intervals, and configured to have 512 channels. In the configuration, measurement points are divided into four groups for every 128 ch.

In the measurement wires of all 512 ch, the related art measurement points 128 ch are connected to the position determination voltage/frequency converters 24 one-to-one as the typical wire electrodes. In FIG. 5, in the total measurement wires, a third channel in the arrangement of the channels is set as a first typical wire electrode, and one typical wire electrode is set in every four channels. Therefore, as illustrated in FIG. 5, 3 ch, 7 ch, . . . , 127 ch, . . . are connected to the position determination voltage/frequency converters 24 as the typical wire electrodes. The precise irradiation position can be determined according to the measurement value information of the typical wire electrodes.

Also, as illustrated in FIG. 5, the remaining 384 channels are connected to the data acquisition voltage/frequency converter 25 as long as those channels are not connected to the position determination voltage/frequency converters 24.

In this situation, the measurement wires at the same positions in the arrangement order of the channels are connected to the same input units of the data acquisition voltage/frequency converter 25 from the respective four groups. With this connection, 384 measurement wires are aggregated into 96 channels in the data acquisition voltage/frequency converter 25 and the monitor signal processing device 22.

If the beam width falls within one graph, the measurement value by the measurement wire at relatively the same position of other groups is a background level. For that reason, in the data acquisition voltage/frequency converter 25, only one measurement value of the plural measurement wires connected to each other is obtained. The large number of measurement values is aggregated by connection to the monitor signal processing devices 22, as a result of which the number of monitor signal processing devices 22 can be reduced as compared with the related art system.

In this embodiment, the total 512 channels are divided into four groups, and the typical wire electrode is extracted, and connected to the position determination voltage/frequency converters 24 for every four channels. However, a configuration having an arbitrary number of channels, arbitrary number of groups, and arbitrary typical wire electrodes is enabled.

The intervals between the respective typical wire electrodes connected to the position determination voltage/frequency converters 24 are set to 4 channels. It is desirable that the intervals between the respective typical wire electrodes are narrower than the beam widths in order to surely detect the passing position of the irradiated ionized particle beam.

Also, the typical wire electrodes are periodically selected from the plural wire electrodes, but the present invention is not limited to this configuration, and arbitrary intervals can be set. As in this embodiment, the typical wire electrodes are periodically selected for every four channels from the plural wire electrodes with the results that portions in which the intervals between the respective typical wire electrodes are unnecessarily narrowed or widened are prevented from occurring, and the beam positions as well as the beam widths and the beam shapes can be stably detected.

Subsequently, a description will be given of a flow of specific processing for detection of the beam position and the beam width in this embodiment with reference to FIG. 6.

In FIG. 6, for simplification of the description, the measurement wires of four groups each having 8 channels are present, to configure a beam monitor having the measurement wires of 32 channels in total. Also, 1 ch, 5 ch, 9 ch, . . . , and 29 ch are connected to the position determination voltage/frequency converters 24 as the typical wire electrodes. The other 2 ch, 3 ch, 4 ch, 6 ch, 7 ch, 8 ch, . . . 30 ch, 31 ch, and 32 ch are connected to the data acquisition voltage/frequency converter 25 together for each of the groups.

In FIG. 6, when the 5 ch to 9 ch of the groups 1 and 2 are irradiated with the beam, the measurement values are transmitted to 5 ch and 9 ch connected to the position determination voltage/frequency converters 24 one-to-one. Also, as described above, the measurement wires are connected to the CPU 8b2-4 within the upstream beam monitor controller 8b1, or the downstream beam monitor controller 8b2 through the voltage/frequency converters 24 and 25 one-to-one. For that reason, in the CPU 8b2-4, it is determined that the measurement values are obtained in the 5 ch and 9 ch portions. In the CPU 8b2-4, it is determined that the distribution of the irradiation beam is present between 5 ch and 9 ch on the basis of the determination result.

In this example, the measurement value data of 6 ch to 8 ch in the group 1 is obtained. In the data acquisition voltage/frequency converter 25, because the measurement wires of the plural groups are connected to the same channel of the voltage/frequency converters together, it is found by which of 6 ch to 8 ch, 14 ch to 16 ch, 22 ch to 24 ch, and 30 ch to 32 ch the measurement values are merely measured with the use of only the processed signal from the data acquisition voltage/frequency converter 25.

However, in the CPU 8b2-4, it can be determined that the positions of the data obtained from the data acquisition voltage/frequency converter 25 are 6 ch to 8 ch according to the determination that the distribution of the irradiation beams is present between 5 ch and 9 ch previously obtained by the position determination voltage/frequency converters 24. With this processing, the distribution of the irradiation beam in the measurement wire portion is determined to implement the calculation of the beam position and the beam width.

Because the beam position and the beam width are calculated on the basis of only information on the real irradiation beam measured in the measurement wire portion, the determination of the irradiation place at the time of miss irradiation is also implemented in the same method as that in the related art system.

As described above, in the beam monitor system and the particle beam irradiation system according to the embodiment of the present invention, the position determination voltage/frequency converters 24 and the data acquisition voltage/frequency converter 25 set one wire electrode from the group of the X-electrode 11d1 and the Y-electrode 11d2 as the typical wire electrode, and receive the detection signal output from the typical wire electrode, and process the detection signal. Also, the data acquisition voltage/frequency converter 25 is connected to all of the wire electrodes other than the typical wire electrodes by the wires of the same number as that of the wire electrodes belonging to the group so as to receive the detection signals output from one wire electrode selected from the respective groups from the same wire. The data acquisition voltage/frequency converter 25 and the data acquisition pulse integration device 8b2-3 receive the detection signals output from all of the wire electrodes other than the typical wire electrodes in the group of the X-electrode 11d1 or the Y-electrode 11d2, and process the detection signal. In addition, the upstream beam monitor controller 8b1 and the downstream beam monitor controller 8b2 obtain the beam position of the ionized particle beam that passes through the wire electrode on the basis of the processed signals from the first position determination pulse integration device 8b2-1 and the second position determination pulse integration device 8b2-2. The upstream beam monitor controller 8b1 and the downstream beam monitor controller 8b2 then obtain the beam width of the ionized particle beam that passes through the wire electrode on the basis of the information on the obtained beam position, the processed signals from the first position determination pulse integration device 8b2-1 and the second position determination pulse integration device 8b2-2, and the processed signal from the data acquisition pulse integration device 8b2-3.

Because the channels used for calculation of the position and the beam width of the ionized particle beam is restricted, there is no need to prepare the amplifier and the signal processing device compatible with all of the channels for the purpose of improving the measurement precision determining the position and the width as in the related art system, and the number of devices in the signal processing system can be reduced. Also, since the typical wire electrodes for position determination are provided, the beam irradiation position can be precisely determined, and the precise beam position and width can be determined according to the measurement values with the simple configuration.

Also, in this embodiment, the upstream beam monitor controller 8b1 and the downstream beam monitor controller 8b2 can obtain the beam position of the ionized particle beam that passes through the wire electrode on the basis of the processed signals from the first position determination pulse integration device 8b2-1, and the second position determination pulse integration device 8b2-2. As a result, there is no need to obtain the beam position of the ionized particle beam passing therethrough on the basis of the irradiation plan position in the treatment planning device 6, the device configuration can be more simplified, and the costs can further be reduced.

Second Embodiment

A description will be given of a beam monitor system and a particle beam irradiation system according to a second embodiment of the present invention with reference to FIG. 7.

FIG. 7 is a flowchart of a control of ionized particle beam irradiation by a raster scan system.

The first embodiment pertains to the particle beam irradiation system having the beam monitor system that monitors the beam position and the beam width in the spot scanning irradiation whereas the particle beam irradiation system according to this embodiment includes a beam monitor system that monitors the beam position and the beam width in the raster scanning irradiation.

The particle beam irradiation system according to this embodiment includes the beam monitor system that monitors the beam position and the beam width in the raster scanning irradiation, which divides an affected area of the patient 13 into plural layers along a beam traveling direction, and scans the ionized particle beam while continuing the irradiation with the ionized particle beam in each of the layers (keeping the beam on).

Hereinafter, a description will be given of the configuration and the operation of the particle beam irradiation system according to this embodiment which are different from those of the first embodiment with reference to FIG. 7.

Upon the completion of preparation of the treatment, a doctor inputs a treatment start signal to the central controller 5 from an input device of the operation terminal 40.

The central controller 5 that receives the treatment start signal transmits a command signal to the accelerator & transportation control system 7.

Then, the accelerator & transportation control system 7 sets the operating parameters corresponding to a layer (first irradiated beam energy information) first irradiated for the synchrotron accelerator 16 and the beam transportation system 2. When the operating parameters of the synchrotron accelerator 16 and the beam transportation system 2 are set to complete the operation start preparation (Step S30), the scanning magnet power supply controller 8c excites the scanning magnet 11b on the basis of the excitation current parameter (Step S31A). After the excitation current corresponding to a first irradiation position has been excited in the scanning magnet 11b, the dose monitor controller 8b3 of the monitor controller 8b starts to monitor the beam dose on the basis of the target dose value for the spot position (Step S32A) and completes pre-irradiation.

When the central controller 5 transmits a beam extraction start command (Step S33), the accelerator & transportation control system 7 starts the ion source, and generates charged particles (protons or heavy particles). The initial accelerator 15 accelerates the charged particles from the ion source, and extracts the charged particles to the synchrotron accelerator 16. The synchrotron accelerator 16 further accelerates the ionized particle beam. The orbiting ionized particle beam is accelerated to target energy, and extracted from the synchrotron accelerator 16 to the beam transportation system 2. The ionized particle beam reaches the scanning irradiation device 3 through the beam transportation system 2. Further, the ionized particle beam travels within the irradiation nozzle 11 along the beam axis, and passes through the upstream beam monitor 11a, the scanning magnet 11b, the dose monitor 11c, and the downstream beam monitor 11d. The affected area of the patient 13 is irradiated with the ionized particle beam extracted from the irradiation nozzle 11.

The dose monitor controller 8b3 receives the measurement data measured by the dose monitor 11c to process the measurement data, and obtains the irradiation dose of each irradiation position. The dose monitor controller 8b3 continues the irradiation of the ionized particle beam until the irradiation dose value of a first irradiation position reaches a target dose value. If the dose monitor controller 8b3 determines that the irradiation dose value reaches the target dose value, the dose monitor controller 8b3 outputs an irradiation completion signal to the central controller 5 (Step S34).

First detection data detected by the upstream beam monitor 11a is captured by the upstream beam monitor controller 8b1, and second detection data detected by the downstream beam monitor 11d is captured by the downstream beam monitor controller 8b2. Then, the position and the beam width of the irradiated ionized particle beam are obtained (Step S35A). The arithmetic processing is completed, and if no error is present in the position and the beam width of the beam (if it is determined that the beam position falls within the allowable beam position, and the beam width falls within the allowable beam width), it is determined whether the irradiation position of irradiation expired is a last irradiation position within the layer, or not. If it is determined that the irradiation position of irradiation expired is not the last irradiation position (no), the scanning magnet power supply controller 8c sets the spot scanning magnet on the basis of the excitation current parameter (Step S35B), and the monitor controller 8b sets the spot dose target value (Step S35C). The control flow 37A from the determination step S34 of the dose expired to the determination of whether the spot is last, or not, is repetitively conducted until it is determined that the irradiation spot of irradiation expired is the last spot position within the layer (until determination of "yes").

If the irradiation of all the spots within the layer has been completed, the central controller 5 determines whether the layer completely irradiated is a last layer of the patient 13, or not (Step S36A). If the layer is not last (no), the central controller 5 transmits a command signal to the accelerator & transportation control system 7. The accelerator & transportation control system 7 sets the operating parameter corresponding to the layer to be next irradiated for the synchrotron accelerator 16 and the beam transportation system 2, and starts a next operation preparation (Step S30).

This control flow 38A is repeated until all of the layers have been completely irradiated. If all of the spots and all of the layers have been completely irradiated, the treatment is completed 39.

In the above flow, the upstream beam monitor controller 8b1 and the downstream beam monitor controller 8b2 implement the same processing as that in the first embodiment.

As described above, the particle beam irradiation system according to this embodiment realizes the raster scanning irradiation that changes the irradiation position in a state where the ionized particle beam is extracted, and irradiates the patient with the beam.

The beam monitor system and the particle beam irradiation system according to the second embodiment of the present invention can obtain substantially the same advantages as those in the above-mentioned beam, monitor system and particle beam irradiation system according to the first embodiment.

That is, the monitor system can be constructed with the simple configuration, and the monitor system low in the costs and high in the reliability can be realized.

<Others>

The present invention is not limited to the above embodiment, but can be performed with various modifications and applications. The above-mentioned embodiments have been described in detail for facilitating to understand the present invention, and the present invention is not always limited to the inclusion of all the configurations described above.

For example, the channels, the segments, and the groups of the monitor can be configured by arbitrary numbers.

Also, in this embodiment, the signal processing device is configured by the digital monitor signal processing device including the voltage/frequency converter and the pulse counter, but may be configured by a circuit that integrates charge, converts the charge into voltage, and output the voltage, or an analog monitor signal processing device that converts a current into a voltage, and outputs the voltage.

Further, a case in which the signal processing device and the beam monitor controller are mounted on separate devices is illustrated, but can be mounted on the same device.

What is claimed is:

1. A beam monitor system, comprising:
   collection electrodes that include a plurality of groups each having a plurality of adjacent wire electrodes, and detect an ionized particle beam passing therethrough;
   a first signal processing device that sets one wire electrode in the groups of the collection electrodes as a typical wire electrode, receives a detection signal output from the typical wire electrode to process the signal; and
   a beam monitor controller that obtains a beam position of the ionized particle beam that has passed through the wire electrodes on the basis of a processed signal from the first signal processing device.

2. The beam monitor system according to claim 1, further comprising: a second signal processing device that receives detection signals output from all of the wire electrodes other than the typical wire electrode in the groups of the collection electrodes to process the signals,
   wherein the second signal processing device is connected to all of the wire electrodes other than the typical wire electrode by wires of the same number as that of the wiring electrode belonging to the groups so as to receive the detection signal output from one wire electrode selected from each of the groups from the same wire, and
   wherein the beam monitor controller obtains a beam width of the ionized particle beam that passes through the wire electrode on the basis of information on the obtained beam position, the processed signal from the second signal processing device, and the processed signal from the first signal processing device.

3. A particle beam irradiation system comprising the beam monitor system according to claim 2.

4. The beam monitor system according to claim 1, wherein the beam monitor controller obtains the beam position of the ionized particle beam that passes through the wire electrodes on the basis of only the processed signal from the first signal processing device.

5. A particle beam irradiation system comprising the beam monitor system according to claim 4.

6. The beam monitor system according to claim 1, wherein an interval between the respective typical wire electrodes is narrower than the beam width of the ionized particle beam.

7. A particle beam irradiation system comprising the beam monitor system according to claim 6.

8. The beam monitor system according to claim 1, wherein the typical wire electrode of the collection electrodes is periodically selected from the plurality of wire electrodes.

9. A particle beam irradiation system comprising the beam monitor system according to claim 8.

10. A particle beam irradiation system comprising the beam monitor system according to claim 1.

* * * * *